(12) United States Patent
Ferrante et al.

(10) Patent No.: US 7,887,537 B2
(45) Date of Patent: Feb. 15, 2011

(54) EXTERNAL FIXATION SYSTEM

(75) Inventors: Joseph Ferrante, Bartlett, TN (US);
Anthony James, Bartlett, TN (US);
David Castleman, Bartlett, TN (US);
Gene Edward Austin, Bartlett, TN (US);
Kenneth Nelson, Memphis, TN (US);
Kelley N. Grusin, Germantown, TX (US)

(73) Assignee: Smith & Nephew, Inc. (GB)

( * ) Notice: Subject to any disclaimer, the term of this patent is extended or adjusted under 35 U.S.C. 154(b) by 1725 days.

(21) Appl. No.: 10/503,453

(22) PCT Filed: Jan. 30, 2003

(86) PCT No.: PCT/US03/02712

§ 371 (c)(1),
(2), (4) Date: Feb. 14, 2005

(87) PCT Pub. No.: WO03/065911

PCT Pub. Date: Aug. 14, 2003

(65) Prior Publication Data

US 2005/0119656 A1    Jun. 2, 2005

(51) Int. Cl.
*A61B 17/00* (2006.01)
(52) U.S. Cl. .................. 606/59; 606/252; 606/56; 606/276; 606/277; 606/278; 24/490; 24/494; 24/515
(58) Field of Classification Search .......... 606/56, 606/59, 260, 276–8, 324, 252; 24/20 S, 30.5 S, 24/33 R, 67.3, 67.7, 68 A, 68 T, 69 TS, 71 T, 24/132 R, 134 R, 136 R, 136 K, 268, 334, 24/336, 385, 437, 438, 477, 490, 492, 494, 24/498, 501, 504, 509, 513, 515–517, 523, 24/535, 536, 538, 544, 134 L
See application file for complete search history.

(56) References Cited

U.S. PATENT DOCUMENTS 554,284 A   2/1896   Lorang (Continued)

FOREIGN PATENT DOCUMENTS

CH         303453        11/1954

(Continued)

OTHER PUBLICATIONS

U.S. Appl. No. 10/172,654, filed Jun. 14, 2002, Ferrante, et al.

(Continued)

*Primary Examiner*—Thomas C Barrett
*Assistant Examiner*—David W Bates
(74) *Attorney, Agent, or Firm*—David Warmbold; David Chambers

(57) ABSTRACT

An external fixation system having a fixation component (20) comprising: a) a first capture member (24) adapted to capture a second element (26) of an orthopedic fixation system; and (b) a second capture member (22) adapted to capture a second element (28) of an orthopedic fixation system and coupled to the first capture member such that the coupling (86,94,110) allows the first capture member and the second capture member to rotate about three axes relative to each other element and move along that axis; wherein the coupling is adapted to secure the first and the second capture members from rotation with an activation (100); and wherein the second capture member is adapted to capture the second element by snapping onto the second element from substantially perpendicular to longitudinal axis of the second element

16 Claims, 14 Drawing Sheets

U.S. PATENT DOCUMENTS

| | | | |
|---|---|---|---|
| 575,631 A | 1/1897 | Brooks | |
| 1,271,792 A | 7/1918 | Standish | |
| 1,563,242 A | 11/1925 | Tweit | |
| 2,250,417 A | 7/1941 | Ettinger | |
| 2,251,209 A | 7/1941 | Stader | |
| 2,346,346 A | 4/1944 | Anderson | |
| 2,391,537 A | 12/1945 | Anderson | |
| 2,391,693 A | 12/1945 | Ettinger | |
| 2,393,694 A | 1/1946 | Kirschner | |
| 2,393,831 A | 1/1946 | Stader | |
| 2,427,128 A | 9/1947 | Ettinger | |
| 2,774,271 A | 12/1956 | Mano | |
| 2,876,027 A | 3/1959 | Sulmonetti | |
| 2,932,029 A | 4/1960 | Nicolo | |
| 3,044,512 A | 7/1962 | Jones | |
| 3,154,331 A | 10/1964 | Engelhardt | |
| 3,195,380 A | 7/1965 | Bicks | |
| 3,336,642 A * | 8/1967 | Armacost | 24/523 |
| 3,509,882 A | 5/1970 | Blake | |
| 3,828,791 A | 8/1974 | Santos | |
| 3,961,854 A | 6/1976 | Jaquet | |
| 4,135,505 A | 1/1979 | Day | |
| 4,170,990 A | 10/1979 | Baumgart et al. | |
| 4,187,840 A | 2/1980 | Watanabe | |
| 4,227,826 A | 10/1980 | Conrad | |
| 4,364,381 A | 12/1982 | Sher et al. | |
| 4,475,546 A | 10/1984 | Patton | |
| 4,483,334 A | 11/1984 | Murray | |
| RE31,809 E | 1/1985 | Danieletto et al. | |
| 4,548,199 A | 10/1985 | Agee | |
| 4,570,625 A | 2/1986 | Harris et al. | |
| 4,611,586 A | 9/1986 | Agee et al. | |
| 4,620,533 A | 11/1986 | Mears | |
| 4,635,634 A | 1/1987 | Santos | |
| 4,666,109 A | 5/1987 | Fallon et al. | |
| 4,696,293 A | 9/1987 | Ciullo | |
| 4,700,437 A | 10/1987 | Hoshino | |
| 4,707,891 A * | 11/1987 | Chidester | 24/136 R |
| 4,730,608 A | 3/1988 | Schlein | |
| 4,785,694 A | 11/1988 | Burmester | |
| 4,848,368 A | 7/1989 | Kronner | |
| 4,922,856 A | 5/1990 | Sweeney, Jr. | |
| 4,998,935 A | 3/1991 | Pennig | |
| 5,062,844 A | 11/1991 | Jamison et al. | |
| 5,152,280 A | 10/1992 | Danieli | |
| 5,160,335 A | 11/1992 | Wagenknecht | |
| 5,167,725 A | 12/1992 | Clark et al. | |
| 5,207,676 A | 5/1993 | Canadell et al. | |
| 5,219,349 A | 6/1993 | Krag et al. | |
| 5,304,177 A | 4/1994 | Pennig | |
| 5,376,090 A | 12/1994 | Pennig | |
| 5,403,313 A | 4/1995 | Lin | |
| 5,405,347 A | 4/1995 | Lee et al. | |
| RE34,985 E | 6/1995 | Pennig | |
| 5,429,637 A | 7/1995 | Hardy | |
| 5,437,666 A | 8/1995 | Tepic et al. | |
| 5,443,465 A | 8/1995 | Pennig | |
| 5,451,225 A | 9/1995 | Ross, Jr. et al. | |
| 5,451,226 A | 9/1995 | Pfeil et al. | |
| 5,507,760 A | 4/1996 | Wynne et al. | |
| 5,545,162 A | 8/1996 | Huebner | |
| 5,586,983 A | 12/1996 | Sanders et al. | |
| 5,622,648 A | 4/1997 | Parri et al. | |
| 5,624,447 A | 4/1997 | Myers | |
| 5,658,283 A | 8/1997 | Huebner | |
| 5,662,648 A | 9/1997 | Faccioli et al. | |
| 5,662,649 A | 9/1997 | Huebner | |
| 5,662,650 A | 9/1997 | Bailey et al. | |
| 5,683,389 A | 11/1997 | Orsak | |
| 5,690,633 A | 11/1997 | Taylor et al. | |
| 5,702,389 A | 12/1997 | Taylor et al. | |
| 5,707,370 A | 1/1998 | Berki et al. | |
| 5,709,685 A | 1/1998 | Dombrowski et al. | |
| 5,728,095 A | 3/1998 | Taylor et al. | |
| 5,728,096 A | 3/1998 | Faccioli et al. | |
| 5,738,684 A | 4/1998 | Thomas et al. | |
| 5,741,252 A | 4/1998 | Mazzio et al. | |
| 5,743,898 A | 4/1998 | Bailey et al. | |
| 5,746,741 A | 5/1998 | Kraus et al. | |
| 5,752,954 A | 5/1998 | Mata et al. | |
| 5,788,695 A | 8/1998 | Richardson | |
| 5,810,817 A | 9/1998 | Roussouly et al. | |
| 5,823,486 A | 10/1998 | Smith et al. | |
| 5,827,282 A | 10/1998 | Pennig | |
| 5,891,143 A | 4/1999 | Taylor et al. | |
| 5,891,144 A | 4/1999 | Mata et al. | |
| 5,897,087 A * | 4/1999 | Farley | 248/229.21 |
| 5,931,837 A | 8/1999 | Marsh et al. | |
| 5,968,043 A | 10/1999 | Ross et al. | |
| 5,971,984 A | 10/1999 | Taylor et al. | |
| 5,976,134 A | 11/1999 | Huebner | |
| 5,997,537 A | 12/1999 | Walulik | |
| 6,010,501 A | 1/2000 | Raskin et al. | |
| 6,024,745 A | 2/2000 | Paccioli et al. | |
| 6,030,386 A | 2/2000 | Taylor et al. | |
| 6,036,691 A | 3/2000 | Richardson | |
| 6,066,142 A | 5/2000 | Serbousek et al. | |
| 6,080,153 A | 6/2000 | Mata et al. | |
| 6,129,727 A | 10/2000 | Austin et al. | |
| 6,168,595 B1 | 1/2001 | Durham et al. | |
| 6,171,308 B1 | 1/2001 | Bailey et al. | |
| 6,203,575 B1 | 3/2001 | Farey | |
| 6,217,577 B1 | 4/2001 | Hofmann | |
| 6,221,072 B1 | 4/2001 | Termaten | |
| 6,238,400 B1 | 5/2001 | Bays | |
| 6,342,054 B1 | 1/2002 | Mata | |
| 6,386,786 B1 | 5/2002 | Perlman et al. | |
| 6,461,358 B1 | 10/2002 | Faccioli et al. | |
| 6,491,694 B1 | 12/2002 | Orsak | |
| 6,503,340 B1 | 1/2003 | Gold et al. | |
| 6,613,049 B2 | 9/2003 | Winquist et al. | |
| 6,616,664 B2 * | 9/2003 | Walulik et al. | 606/57 |
| 6,709,433 B1 | 3/2004 | Schoenefeld | |
| 7,207,992 B2 * | 4/2007 | Ritland | 606/86 A |
| 2001/0049526 A1 | 12/2001 | Venturini et al. | |
| 2002/0026190 A1 | 2/2002 | Walulik et al. | |
| 2002/0049446 A1 | 4/2002 | Harkey, III et al. | |
| 2002/0077629 A1 | 6/2002 | Hoffman et al. | |
| 2002/0165543 A1 | 11/2002 | Winquist et al. | |
| 2003/0125736 A1 | 7/2003 | Venturini et al. | |
| 2003/0149429 A1 | 8/2003 | Ferrante et al. | |
| 2003/0149430 A1 | 8/2003 | Ferrante et al. | |
| 2004/0138659 A1 | 7/2004 | Austin | |
| 2005/0245939 A1 | 11/2005 | Ferrante et al. | |
| 2005/0261680 A1 | 11/2005 | Draper | |

FOREIGN PATENT DOCUMENTS

| | | |
|---|---|---|
| CH | 02 709/94-3 | 9/1994 |
| DE | 375 151 | 5/1923 |
| DE | 1 935 977 | 2/1971 |
| DE | 1 603 999 | 5/1971 |
| DE | 27 45 504 A1 | 4/1979 |
| DE | 38 05 178 A1 | 8/1989 |
| DE | 38 23 746 A1 | 1/1990 |
| DE | 42 38 582 A1 | 5/1994 |
| DE | 295 12 917 U1 | 11/1995 |
| EP | 0 524 441 A1 | 1/1993 |
| EP | 0 611 007 A1 | 8/1994 |
| EP | 0 700 664 A1 | 3/1996 |
| EP | 1 021 992 A2 | 7/2000 |
| FR | 2 665 353 A | 2/1992 |
| NO | 25934 | 6/1915 |
| SU | 167008 | 11/1964 |

| | | |
|---|---|---|
| SU | 1491-492 A1 | 8/1986 |
| SU | 1572590 A1 | 6/1990 |
| WO | WO 88/01152 | 2/1988 |
| WO | WO 88/03395 | 5/1988 |
| WO | WO 94/18898 | 9/1994 |
| WO | WO 96/12443 | 5/1996 |
| WO | WO 97/10775 | 3/1997 |
| WO | WO 97/16128 | 5/1997 |
| WO | WO 98/36698 | 8/1998 |
| WO | WO 99/22661 | 5/1999 |
| WO | WO 99/29247 | 6/1999 |
| WO | WO 00/40163 | 7/2000 |
| WO | WO 03/065911 | 8/2003 |
| WO | WO 03/105704 A1 | 12/2003 |
| WO | WO 2004/062514 A1 | 7/2004 |

OTHER PUBLICATIONS

U.S. Appl. No. 10/067,052, filed Feb. 4, 2002, Ferrante, et al.
Agee, "External Fixation: Technical Advances Based Upon Multiplanar Ligamentotaxis," *Orthopedic Clinics of North America*, 24(2) (Apr. 1993).
Hoffmann II External Fixation System, 3 pages (Oct. 15, 2001) http:--www.osteonics.com-howmedica-products-frames-prod2p.
"Epiphyseal Distraction Hemichondrodiatasis," by Roberto Aldegheri, et al., *Clinical Orthopaedics and Related Research*, No. 241, pp. 128-136, Apr. 1989.
"Use of an Articulated External Fixator for Fractures of the Tibial Plafond," *The Journal of Bone and Joint Surgery*, pp. 1498-1509, 1995.
Articulated External Fixation of Tibial Pilon Fractures: Effects on Ankle and Fragment Kinematics by D. C. Fitzpatrick, et al., $40^{th}$ Annual Meeting, Orthopaedic Research Society, Feb. 21-24, 1994, New Orleans, Louisiana, one page.
ORTHOFIX Brochure entitled "Ankle Fusion Technique," one page, undated.
ORTHOFIX Brochure entitled "Arthrodiatasis Articulated Joint Distraction" by Dr. G. Trivella and Prof. M. Saleh, 8 pages (undated).
ORTHOFIX Operative Technique Brochure entitled "Distal Tibial and Pilon Fractures," by Dr. J. L. Marsh and Dr. F. Lavini, pp. 1-20, Oct. 16, 2002.
*Orthopedics Today*, vol. 14, No. 11, "Swedish cartilage repiart study offers hope, but more research is needed," pp. 1 and 43, Nov. 1994.
Patent Abstracts of Japan, vol. 017, No. 270 (C-1063), May 26, 1993 & JP 05 007604 A (Nagano Keiki Seisakusho), Jan. 19, 1993.
Smith & Nephew Brochure entitled "Only from Smith & Nephew The Original Ilizarov System," 14 pages (Jan. 1999).
Hontzsch, et al., 'The New Open Universal Clamp for the External Fixator Tubular System of the AO/ASIF,' *AO/ASIF Dialogue*, VII(1):6-9 (Jun. 1994).
Hontzsch, et al. 'Neue offene Universalbacke fur das Fixateur externe-Rohrsystem der AO,' *Aktuelle Traumatologie*, 24:24-30 (1994).
Brochure entitled "Hoffmann® II Compact™, External Fixation System," Stryker® Trauma, Stryker Corporation, 20 pages, 2001.
Brochure entitled "Hoffmann® II, External Fixation System," Stryker® Trauma, Stryker Corporation, 24 pages, 2001.
Brochure entitled "Hoffmann® II Compact™, External Fixation System, Technical Guide," Stryker® Trauma, Stryker Corporation, 36 [pages, 2000.
Brochure entitled "Hoffmann® II, External Fixation System, Technical Guide," Stryker® Trauma, Stryker Corporation, 28 pages, 2000.

* cited by examiner

EXTERNAL FIXATION SYSTEM

CROSS REFERENCE TO RELATED APPLICATIONS

This application is the U.S. national phase of International Application No. PCT/US03/02712 filed on Jan. 30, 2003 and published in English as International Publication No. WO 03/065911 A1 on Aug. 14, 2003, which application claims priority to U.S. application Ser. No. 10/172,654 filed on Jun. 14, 2002 which is a continuation-in-part of U.S. application Ser. No. 10/067,052 filed on Feb. 4, 2002, the contents of which are incorporated herein by reference.

FIELD OF THE INVENTION

This invention relates generally to methods, systems, and devices for orthopedic external fixation and more particularly to an external fixation system having an improved fixation component for constructing a stable, adjustable fixation system that cooperates with other systems, and methods of use thereof.

BACKGROUND OF THE INVENTION

Surgeons use external fixation systems regularly to treat certain bony skeletal injuries or conditions, such as acute fractures of the skeleton, soft tissue injuries, delayed union of the skeleton when bones are slow to heal, nonunion of the skeleton when bones have not healed, malunion of broken or fractured bones, congenital deformities resulting in malposition of bone, and bone lengthening, widening, or twisting. Treatment of these conditions often includes stabilization and reduction using an external fixation system. These systems may include a frame comprised of one or more of fixation components and one or more fixation elements. As used herein, fixation component refers to a device for positioning one or more parts of an external fixation system, and fixation element refers to one or more of a bar, rod, wire, or pin used in an external fixation system. Wires may be threaded, beaded, or smooth, and pins may be threaded or smooth. Generally, one or more bone pins or wires are inserted into the tissue and bone and then the remainder of the fixation system is assembled. It is often important that a surgeon is able to place the external fixation system on the patient and then reduce the fracture in an expedited manner. Fracture patterns are infinite and may require the fixation system to move in multiple planes simultaneously in order to stabilize and reduce the fracture properly.

Current external fixation system designs vary, but generally include a mechanism for attaching at least one fixation element to a fixation component to form a construct, or frame, to support a fracture. In general, at least one pin or wire is drilled into the bone. Bone pins typically have one end that is either or both self-drilling and self-tapping, and have a diameter sufficient to resist bending. Bone wires are generally smaller in diameter. Bone pins or wires may be drilled completely through the bone, exiting the skin on the opposite side of the bone, called "transfixation pins," or may extend through the bony skeleton and out only one side of the limb, called "half pins." Current fixation components generally either connect a bar to a bar, a bar to a wire, or a bar to a pin. The frame of an external fixation system may include unilateral bars, which extend along the side of a patient's body, or circumferential or half rings, which encircle a patient's body member entirely or in part. Systems designed to use a circumferential ring or half ring include the ILIZAROV™ brand system and the SPATIAL FRAME™ brand system. The SPATIAL FRAME™ brand system is described in U.S. Pat. No. 5,702,389, which is hereby incorporated by reference. Generally, circumferential and half rings have a rectangular cross-section.

When stabilizing and reducing a fracture using an external fixation system, it is important to properly align the bone fragments. Such alignment requires a fixation component that securely joins the pins and wires to the bars, but that is readily adjustable. In many cases, two pins are inserted below the fracture and two pins are inserted above the fracture. The surgeon then attaches a fixation component to each pin, bridging the fixation components together with rods, or bars. These bars form the frame of the external fixation system. As additional fixation components are added to the system in different planes, the frame becomes less adjustable. Current fixation systems permit a surgeon to choose the positioning of only two fixation components because after placement of two components, additional fixation components will only fit into set positions. During a procedure, it is often necessary to further reduce a fracture, which requires removal of the bars (and loss of positioning) and then replacement of the bars in the frame. Thus, additional reduction is difficult to achieve and requires reestablishment of optimal position. Current systems are also highly dependent on accurate pin or wire placement. For example, if the pins or wires are angled incorrectly, the frame cannot be properly constructed.

One current external fixation component design includes two clamps that rotate in one plane to allow limited manipulation of the external fixation component. One jaw of each clamp of this design includes a toothed chip mechanism that has a surface with teeth similar to a poker chip. The teeth mate and lock when compressed, and thereby resist rotation in one plane after the clamps are in place. This poker chip design requires that the two fixation elements retained by the component are parallel to each other in at least one plane that is parallel to the poker chip surface, so that the angular relationship between the two fixation elements is always zero in that plane. Therefore, this system requires a parallel plane between the pin or wire and bar (or between two bars) for each fixation component This requirement limits the system, as the positioning of each clamp is inhibited. Similar to other current designs, this design becomes substandard when several fixation components are used because it becomes constrained.

In addition, the clamps of many current designs are adjacent a central shaft and are both locked upon tightening of a single screw, further constraining the system. Many current designs also allow for placement of the pins in the pin clamp of a fixation element only from the side and require a bent bar for placement of the system proximate the patient, if it is necessary to conform the system to the patient's anatomy. In addition, current designs use compression to hold the bar or pin in place, and may allow dislodgement of the pin or bar upon application of a great amount of pressure to the system when being placed.

Other prior art designs include circumferential rings or half rings, such as those in the ILIZAROV™ and SPATIAL FRAME™ brand systems. These specialized systems are often used for reduction of a fracture of the proximal tibia or distal femur. Generally, wires connected to half rings are used to stabilize a fracture. These specialized systems do not cooperate with general external fixation systems, and must be used separately.

Thus, there is a need for an external fixation system that provides a greater degree of freedom of rotation of the fixation components and therefore a more flexible frame construct, sequential locking of capture members, allowing greater adjustability, and cooperation with specialized fixation systems.

SUMMARY OF THE INVENTION

An external fixation system according to one embodiment of this invention allows manipulation of an external fixation component in any plane independent of the number of fixation components used, which is provided by the ability of the fixation component to rotate in multiple planes. Further, an improved fixation component according to one embodiment of this invention provides an external fixation system that does not bind or become constricted when numerous fixation components are used, providing the surgeon a stable system that is adjustable.

One embodiment of a fixation component according to this invention includes two capture members, a first capture member adapted to capture a first fixation element and a second capture member adapted to capture a second fixation element. The capture members are coupled such that the coupling allows the first capture member and second capture member to rotate about three axes relative to each other and the second capture member to rotate about one axis of the second fixation element and move along that axis. The coupling is adapted to secure the first and second capture members from rotation and secure the second capture member from rotating about and moving along the axis of the second fixation element with a single activation. The second capture member is adapted to capture the second fixation element by snapping onto the second element from substantially perpendicular to the longitudinal axis of the second element.

One feature of one embodiment of this invention is a fixation component that provides a greater degree of freedom of rotation.

Another feature of one embodiment of this invention is a fixation component that simultaneously locks a capture member to a fixation element and locks the joint between two capture members.

Another feature of one embodiment of this invention is a modular design whereby at least one of the two capture members of a fixation component may be interchangeable with another capture member. For example, if a fixation component has two capture members each for receiving a bar, the two capture members may be separated at the joint, and another capture member, for receiving a pin, may be attached to one of the original two capture members to form a fixation component with one capture member for receiving a bar and the other capture member for receiving a pin.

Yet another feature is a fixation component that allows one capture member to be locked to retain a fixation element without forcing the second capture member also to be locked, allowing additional adjustment of position of the second capture member.

Another feature of one embodiment according to this invention is a fixation component having a locking mechanism that is not dislodged by application pressure.

Yet another feature of one embodiment of this invention is a fixation component that cooperates with specialized fixation systems.

According to the present invention there is provided an external fixation component comprising (a) a first capture member adapted to capture a first element of an orthopedic fixation system; and (b) a second capture member adapted to capture a second element of an orthopedic fixation system and coupled to the first capture member such that the coupling allows the first capture member and the second capture member to rotate about three axes relative to each other and the second capture member to rotate about one axis of the second element and move along that axis; wherein the coupling is adapted to secure the first and second capture members from rotation with an activation; and wherein the second capture member is adapted to capture the second element by snapping onto the second element from substantially perpendicular to the longitudinal axis of the second element.

According to the present invention there is provided a method of treating a skeletal condition or injury using an external fixation system, the method comprising: (a) inserting a first fixation element into a bone; (b) capturing the first fixation element in a first fixation component by snapping onto the first fixation element from substantially perpendicular to the longitudinal axis of the first fixation element, the first fixation component comprising: (i) a first capture member adapted to capture an element of an orthopedic fixation system; and (ii) a second capture member adapted to capture an element of an orthopedic fixation system and coupled to the first capture member such that the coupling allows the first capture member and the second capture member to rotate about three axes relative to each other; wherein the coupling is adapted to secure the first and second capture members from rotation with a single activation; (c) capturing a second fixation element in the first fixation component by snapping onto the second fixation element from substantially perpendicular to the longitudinal axis of the second fixation element; and (d) engaging the single activation to secure the first and second capture members from rotation.

DETAILED DESCRIPTION OF THE INVENTION

Methods, systems, and devices according to this invention seek to provide improved external fixation, including an improved fixation component allowing an increase in freedom of rotation, independent locking of capture members, a more stable, yet more flexible frame, and cooperation with specialized fixation systems. External fixation systems according to embodiments of this invention may include fixation components designed to retain one or more fixation elements. In general, the fixation components either connect a bar to a bar; a bar to a pin; a bar to a wire; or a bar to a circumferential or half ring. Each fixation component generally includes two capture members, and each capture member includes a base and a head.

One embodiment of a fixation component according to this invention includes a first capture member and a second capture member connected by a joint. Each capture member includes a channel, which allows attachment of a fixation element from the side. Prior to being locked down, each fixation element can slide (back and forth) and rotate within the channel providing two degrees of freedom between the fixation element and the capture member. The first and second capture members are connected by a joint that allows each capture member to rotate with respect to the other capture member. The joint also allows rotation of up to 50° in any plane (25° each way), increasing the degree of freedom of rotation. In one embodiment, angulation is limited to 50° due to profile height constraints. However, in another embodiment more angulation may be provided. Thus, each capture member is provided three degrees of rotational freedom relative to the other capture member. An external fixation system including fixation components according to this invention allows movement of the bone along six separate axes, a combination of three orthogonal translational axes and three orthogonal rotational axes.

In one embodiment according to this invention, a fixation component having a unique joint allows simultaneous locking of one capture member and the joint. In addition, one capture member may be locked in place while the second capture member continues to freely rotate. In this manner, the surgeon is able to lock one capture member and continue to rotate the second capture member for final positioning. The surgeon is also able to loosen only one capture member to gain additional reduction, if required, without losing placement, as occurs with current systems when additional reduction is required.

Figure 7:
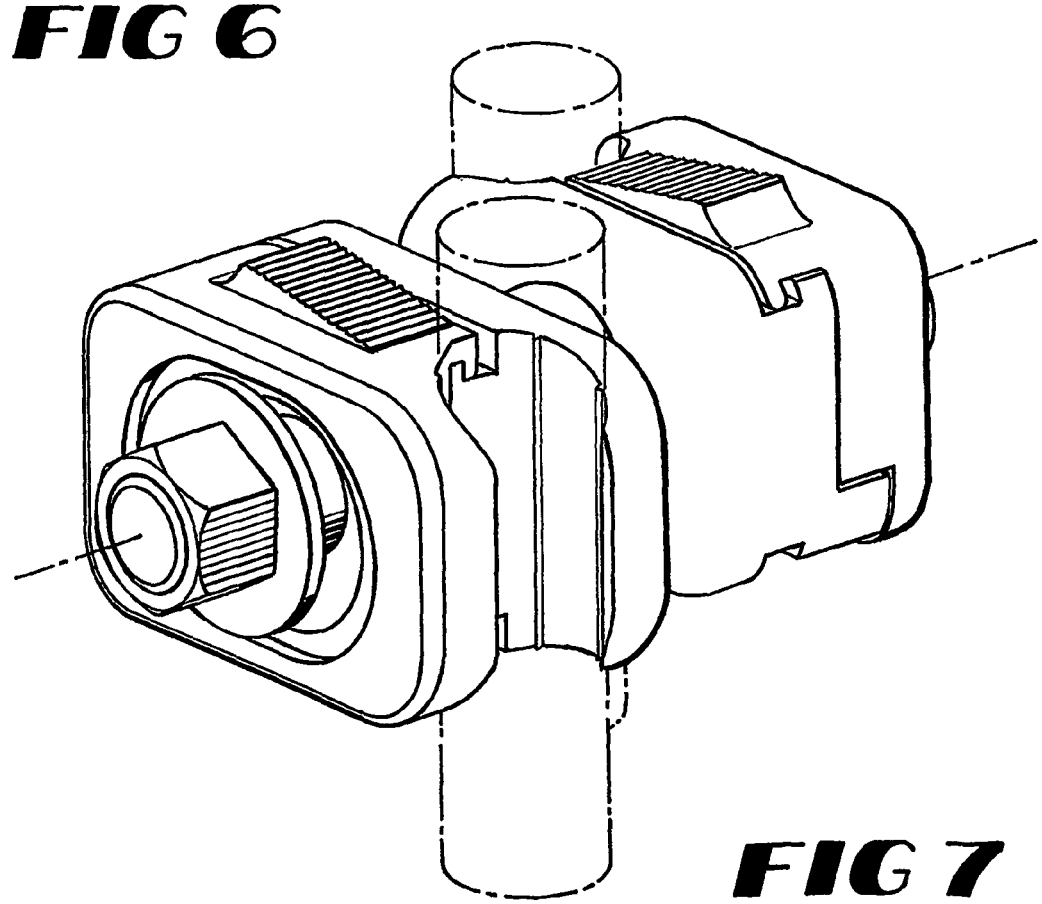
FIG. 7 is a perspective view of a fixation component according to an alternative embodiment of this invention.
Figure 8:
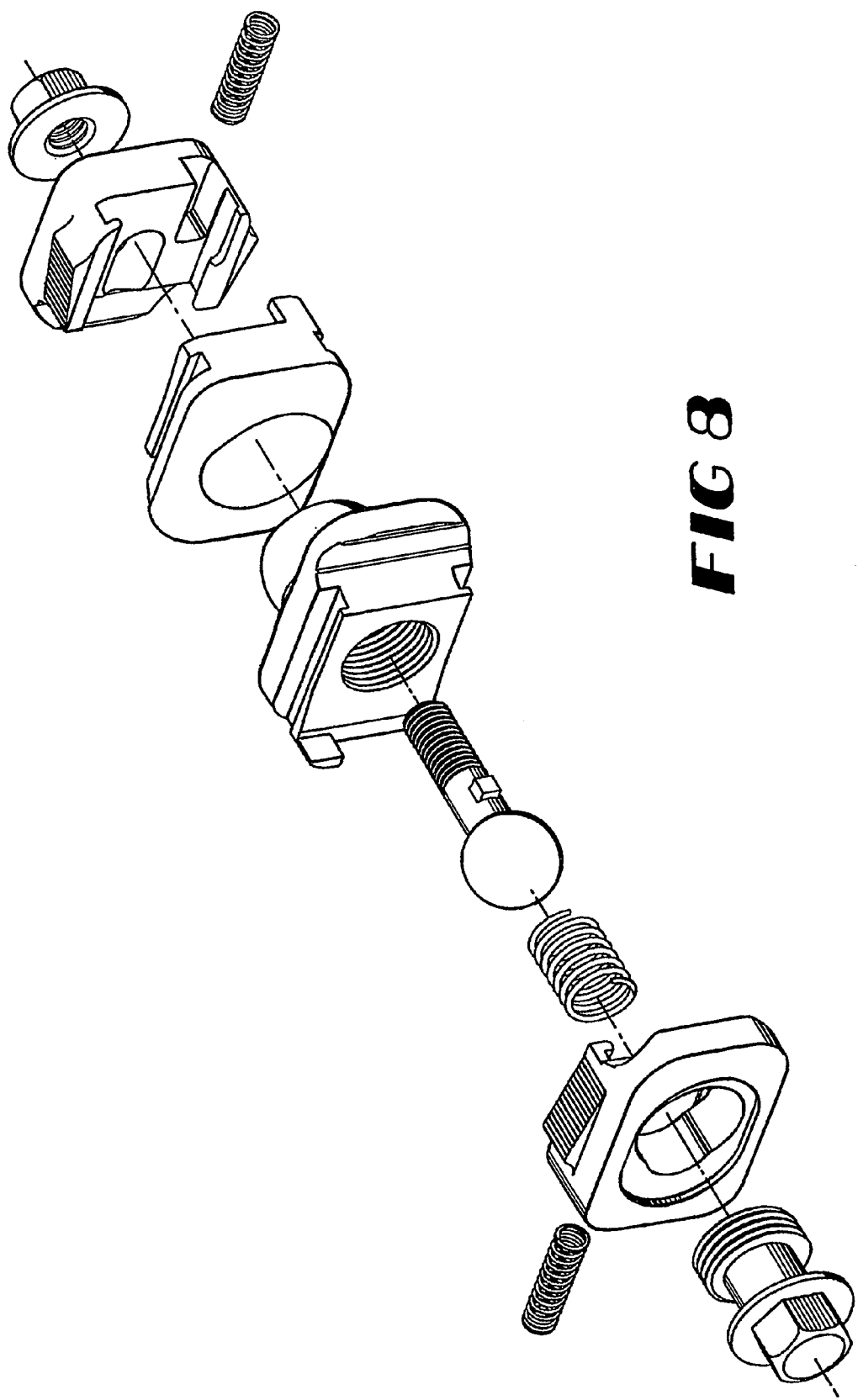
FIG. 8 is an exploded perspective view of the fixation component of FIG. 7.
Figure 9:
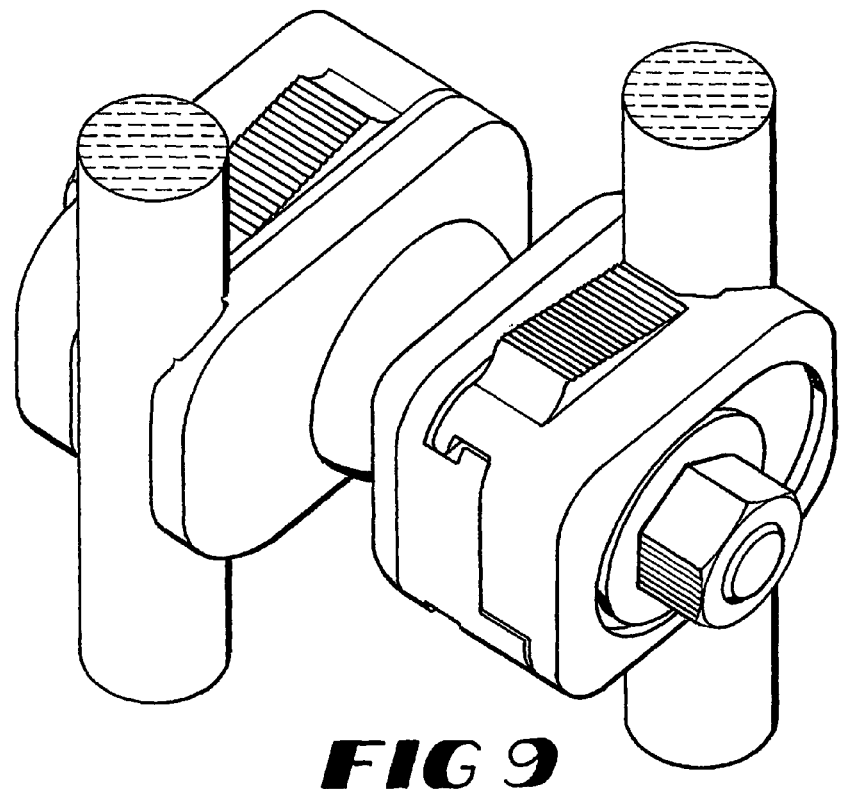
FIG. 9 is a perspective view of the fixation component of FIG. 7, with bars inserted in the capture members.

Consider one example of systems and devices according to this invention. As shown in FIGS. 1-6, a bar-to-pin fixation component 20 includes a first capture member 24 and a second capture member 22. First capture member 24 retains a pin 26, while second capture member 22 is configured to retain a bar 28, as shown in FIG. 3. A base 30 of first capture member 24 includes a groove 32, while a head 34 of first capture member 24 contains a wedge 36, which together are adapted to retain pin 26. Likewise, a base 38 and a head 40 of second capture member 22 include a groove 42 and a wedge 44, together adapted to retain bar 28. In one embodiment, groove 42 of second capture member 22 has splines 46, which provide rotational stability of bar 28 and penetrate the surface of bar 28 when second capture member 22 is tightened. Alternatively, the second capture member may be adapted to retain a pin and the first capture member may be adapted to retain a bar. In an alternative embodiment, both the first and second capture members are configured to retain a bar, as shown in FIGS. 7-9. In another embodiment, one capture member is adapted to retain a wire, while the other capture member is adapted to retain a bar. In another embodiment, the capture members are modular allowing for each capture member to be connected to a similarly designed capture member. Additional embodiments are further described below.

Figure 1:
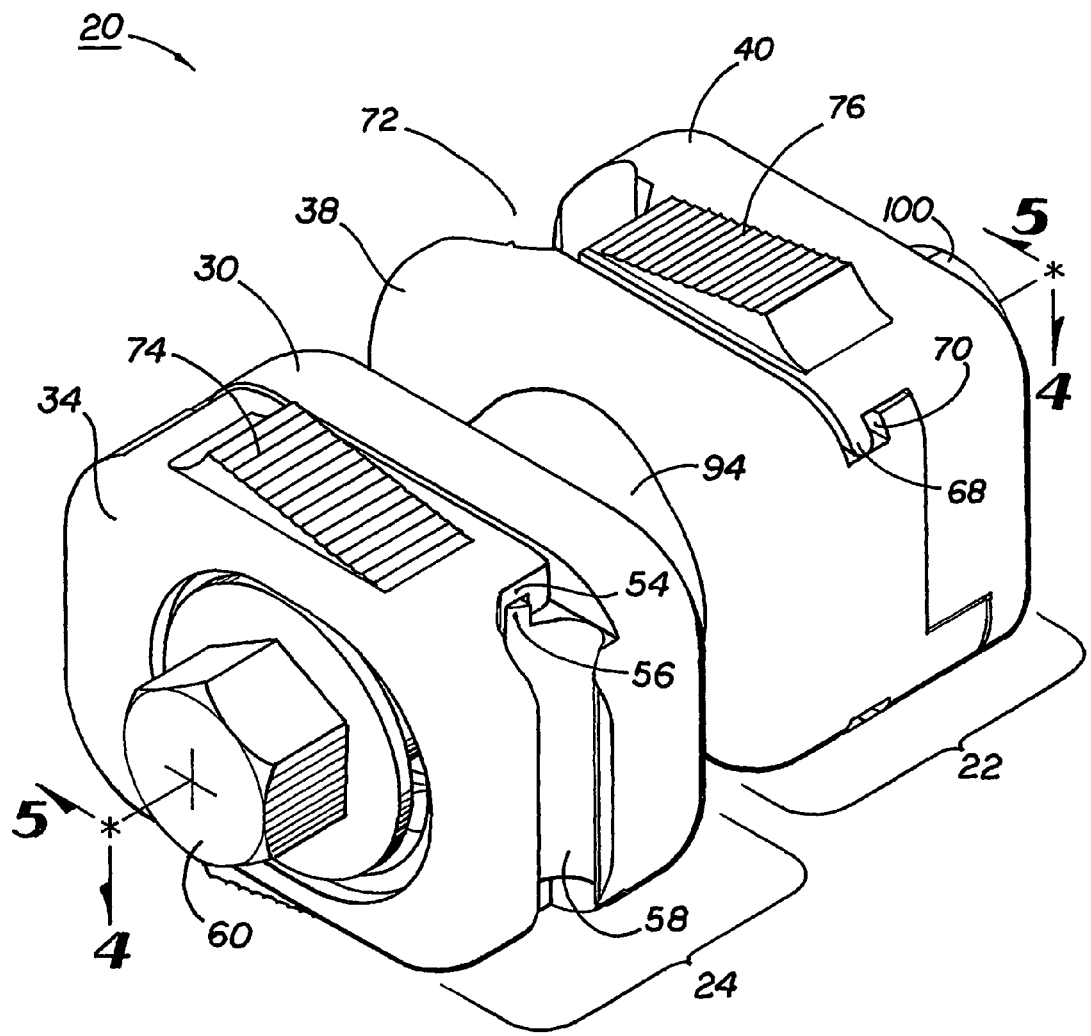
FIG. 1 is a perspective view of a fixation component according to one embodiment of this invention.
Figure 2:
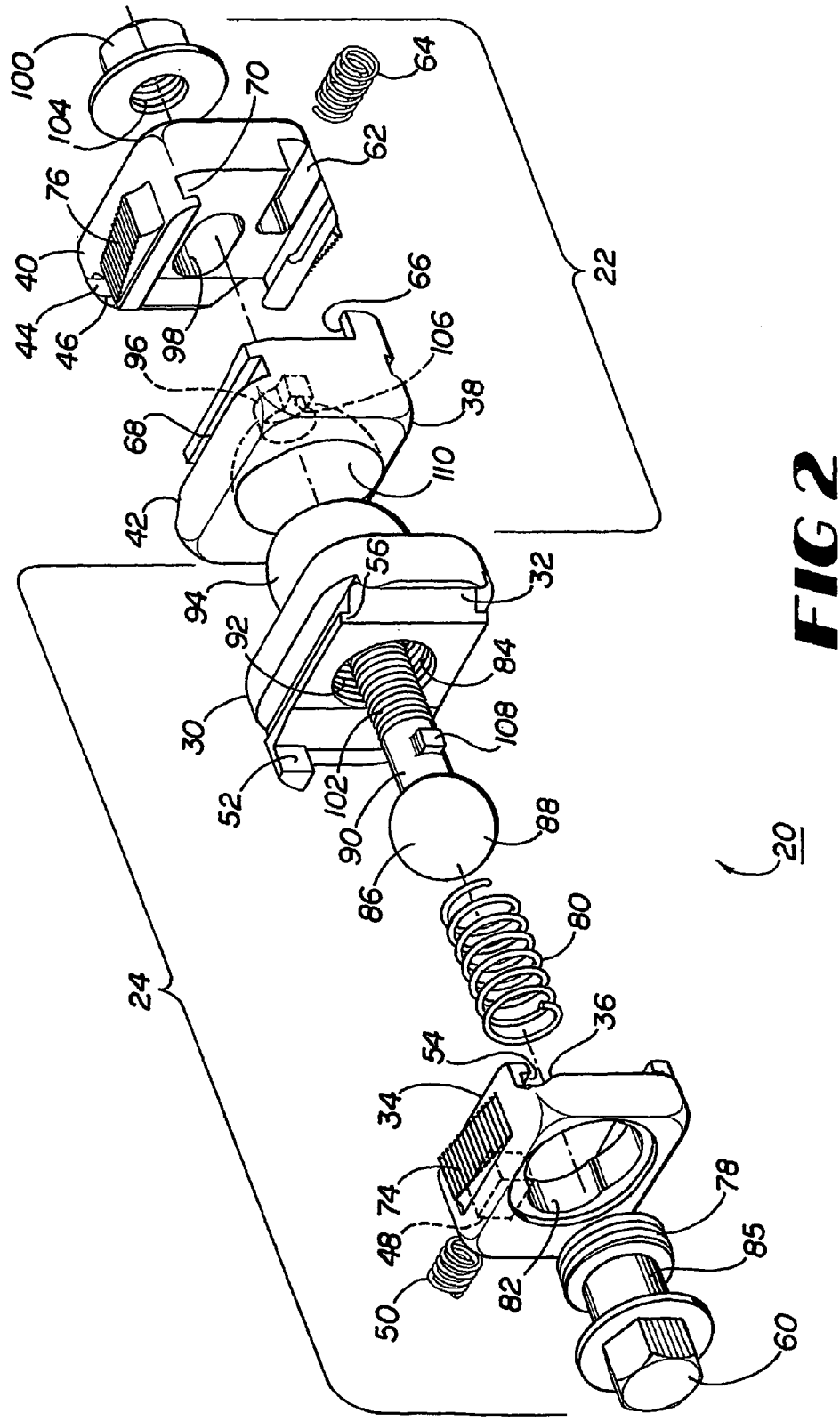
FIG. 2 is an exploded perspective view of the fixation component of FIG. 1.
Figure 3:
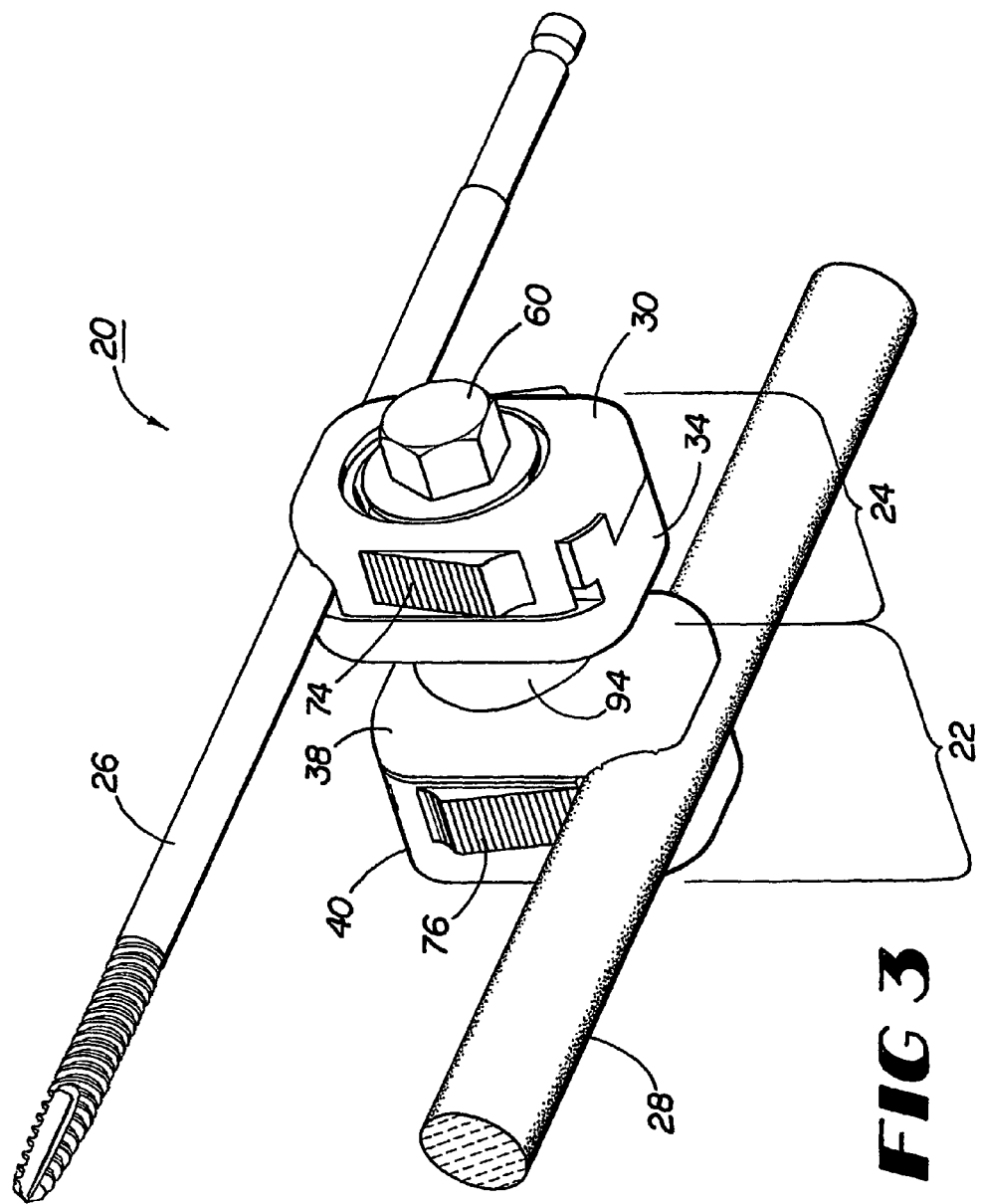
FIG. 3 is a perspective view of the fixation component of FIG. 1 with a pin and bar inserted.

As shown in FIG. 2, head 34 of first capture member 24 has a recess 48 adapted to receive a spring 50, while base 30 of first capture member 24 includes a stop 52. A first track 54 on each side of head 34 slides in a second track 56 on each side of base 30, allowing head 34 and base 30 of first capture member 24 to translate with respect to each other. In an alternative embodiment, second track 56 slides in first track 54. In one embodiment, one of first and second tracks 54, 56 is an L-shaped track, while the other track is shaped to receive the L-shaped track. As a force in a direction perpendicular to the pin is exerted against groove 32 and wedge 36 of first capture member 24, head 34 moves, compressing spring 50 against the extended portion of base 30. Spring 50 compresses until it exerts a force in a direction perpendicular to pin 26 that is equal and opposite to the force exerted against wedge 36. At that point, head 34 stops moving and holds pin 26 in groove 32 and wedge 36, which together form channel 58.

Figure 4:
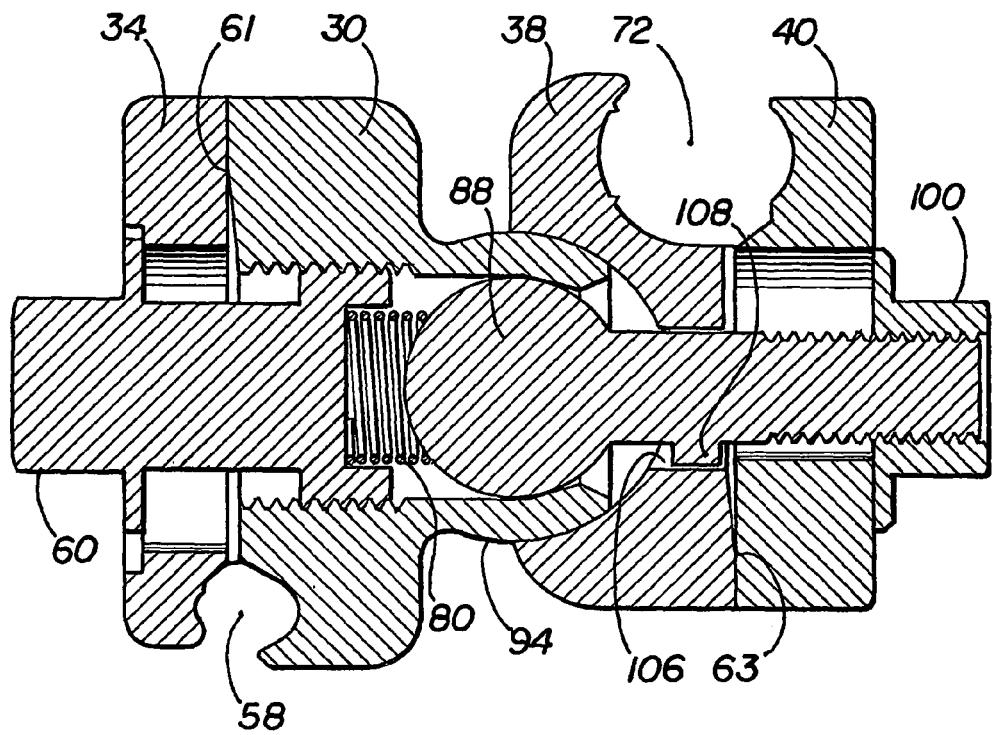
FIG. 4 is a cross-sectional view of the fixation component taken along lines 4-4 in FIG. 1.
Figure 5:
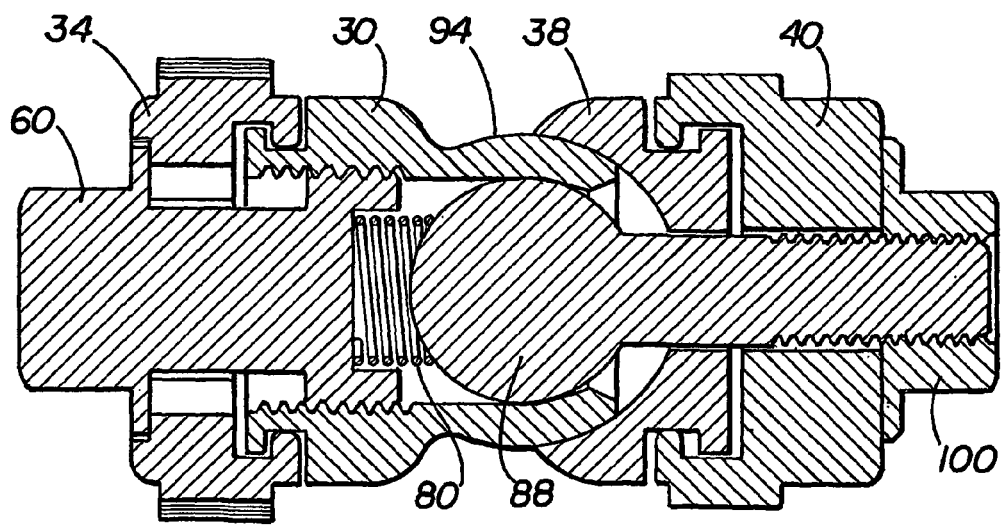
FIG. 5 is a cross-sectional view of the fixation component taken along lines 5-5 in FIG. 1.
Figure 6:
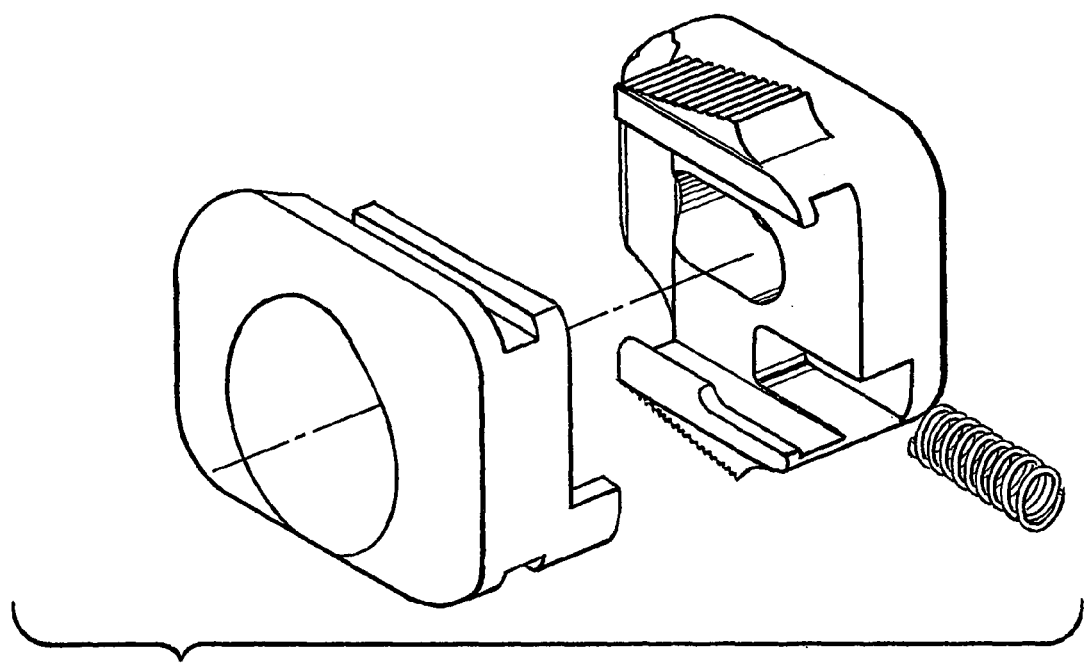
FIG. 6 is an exploded perspective view of the second capture member of FIG. 1.

The angular position of channel 58 is set by tightening a first fastener 60. Prior to tightening of first fastener 60, the cartridge mechanism, in the loosened state, does not allow pin 26 to passively separate or detach from capture member 24. Base 30 of first capture member 24 includes an elevated portion 61, as shown in FIG. 4, forcing two points of contact between base 30 and head 34 in order to increase the holding power of first capture member 24. Base 38 of second capture member 22 also includes an elevated portion 63, also shown in FIG. 4, which increases the holding power of second capture member 22 in the same manner.

Second capture member 22 also includes a cartridge mechanism for retaining bar 28. Head 40 of second capture member 22 has a recess 62 adapted to receive a spring 64, while base 38 of second capture member 22 includes a stop 66. A first track 68 on each side of head 40 slides in a second track 70 on each side of base 38. In an alternative embodiment, second track 70 slides in first track 68. In one embodiment, one of first and second tracks 68, 70 is an L-shaped track, while the other track is shaped to receive the L-shaped track. Groove 42 and wedge 44 of second capture member form a second capture member channel 72, which receives a bar 28. Bar 28 is retained in second capture member 22 in the same manner as first capture member 24 retains pin 26.

In an alternative embodiment, one or both capture members may include two recesses for receiving two springs and two spring stops. In the embodiments shown, the recess, spring, and stop are located on one side of the capture member. In an alternative embodiment, the recess, spring, and spring stop are in the middle of the capture member, or are on the other side of the capture member. In one embodiment, heads 40 and 34 of capture members 22 and 24, respectively, include grip surfaces 74 and 76 for gripping and sliding heads 40 and 34 in relation to bases 38 and 30, respectively. In one embodiment, grip surfaces 74 and 76 include ridges.

A threaded end 78 of first fastener 60 is adjacent a biasing element, such as a center spring 80, and passes through a keyhole aperture 82 in head 34 of first capture member 24, mating to internal threads 84 in base 30 of first capture member 24. Keyhole aperture 82 of head 34 if first capture member 24 allows a reduced diameter neck 85 of first fastener 60 to translate within the aperture 82. Tightening of first fastener 60 locks first capture member 24 and rigidly retains pin 26. In an alternative embodiment, aperture 82 is circular, or any other suitable shape.

A connector 86 having an end 88 and a shaft 90 extends through a keyhole aperture 92 in base 30 of first capture member 24. In one embodiment, connector 86 is a ball stud, as shown in FIG. 2, having a spherical end. End 88 of connector 86 is received in a planetary member 94 of base 30 of first capture member 24. As used herein, a planetary member refers to an object that is received in another object, and that receives another object within itself. In one embodiment, planetary member 94 is an outer sphere, as shown in the figures. Shaft 90 of connector 86 extends through an aperture 96 in base 38 of second capture member 22 and an aperture 98 in head 40 of second capture member 22, and mates with a second fastener 100. Threads 102 on shaft 90 of connector 86 mate with internal threads 104 of second fastener 100.

A slot 106 in aperture 96 of base 38 of second capture member 22 is adapted to receive a key 108 on shaft 90 of connector 86. Key 108 and slot 106 thus prevent rotation of connector 86 within second capture member 22. In another embodiment, any suitable mechanism for preventing rotation of the connector is used. In other words, the connector fits through the base of the first capture member and the end is received in the planetary member of the base, while the shaft of the connector extends through both the base and head of the second capture member and threads to a second fastener. A planetary member, for example outer sphere 94, fits within a cooperating surface 110, which is machined into the one side of base 38 of second capture member 22. Tightening of second fastener 100 on second capture member 22 draws connector 86 into planetary member 94, locking the second capture member and the joint to make it rigid. In one embodiment, one or both of the planetary member and cooperating surface may be tapered. For example, a taper of 10°, 15°, 20°, or 30° may be used on each.

The joint mechanism described above allows the second capture member to rotate with respect to the planetary member of the first capture member, and allows the first capture member to grasp and lock a pin while permitting the second capture member to continue to rotate. Independent tightening of the capture members provides the surgeon flexibility to snap a fixation element to a capture member and then to manipulate the second capture member before locking the second capture member in order to achieve a more stable frame. In this manner, independent tightening of each capture member of the external fixation component allows more precise angular positioning. Alternative embodiments of a joint mechanism between two capture members are described below with reference to FIGS. 14-19.

Other embodiments, such as a bar-to-bar fixation component, shown in FIGS. 7-9, and a bar-to-wire fixation component, also may contribute to a more stable, more adjustable external fixation system. These embodiments function similarly to the bar-to-pin fixation component, with the capture members having a wedge and groove adapted to form a channel sized for receiving either a bar or a wire, depending on the component.

In one embodiment, a cartridge locking of the pin and bar is provided, as described above. However, in alternative embodiments, other one-piece designs may be used. For example, a solid piece of aluminum metal having the shape of the two part head and base cartridge construct of the two capture members may be used. This one-piece design includes a channel in each one piece capture member and a slot that extends close to the rear portion of the capture member. The slot causes the material to behave similar to a spring and allows the capture member to open when pressure is placed against it, so that a fixation element may be snapped into place in the channel.

Several mechanisms may be used to improve the locking capabilities of the joint. Coatings or elastic materials or alternate taper shapes may be applied to any of the articulating surfaces. For example, coatings or elastic materials or alternate taper shapes may be applied to one or both of the planetary member and cooperating surface so that a textured surface on either or both improves locking. In one embodiment, the cooperating surface is coated with SC729, a coating manufactured by Hitemco. In this embodiment, the cooperating surface is very rough and is made from tungsten cobalt carbide. In this embodiment, the value for slip increases to about 240 in.-lb., from about 140 in.-lb. without the coating. In an alternative embodiment, a mechanical locking pattern is applied. For example, splines and dimples may be added to one or both of planetary member and cooperating surface, providing teeth to grab when locking, thereby improving the locking function. A 30 degree chosen taper configuration on the inside of the planetary member mating surface uses a taper design to achieve torque strength of up to 200 in.-lb.

In an alternative embodiment, a fixation component is designed for attachment to a circumferential external fixator system, such as an ILIZAROV™ brand system, a SPATLAL FRAME™ brand system, or other spatial frame, to achieve a hybrid external construct. In this embodiment, shown in FIGS. 10-11, the fixation component includes a capture member for retaining a bar and a capture member for retaining a half or circumferential ring having a generally rectangular cross-section. Use of a fixation component having a capture member for retaining a ring allows a surgeon to create a hybrid frame, using both a standard external fixation system and a system that includes a circumferential external frame. This hybrid system is very useful in adapting a system for treating a shaft fracture, or typical in-line fracture, to one for treating a plateau fracture, which is a fracture in a joint space.

Figure 10:
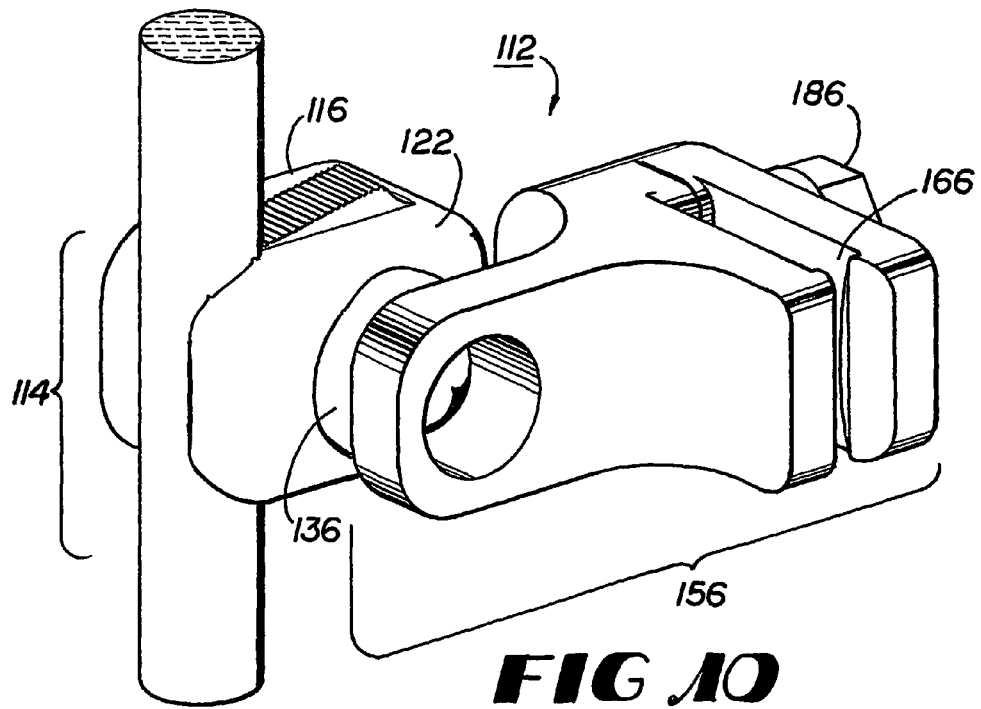
FIG. 10 is a perspective view of a fixation component according to an alternative embodiment of this invention.
Figure 11:
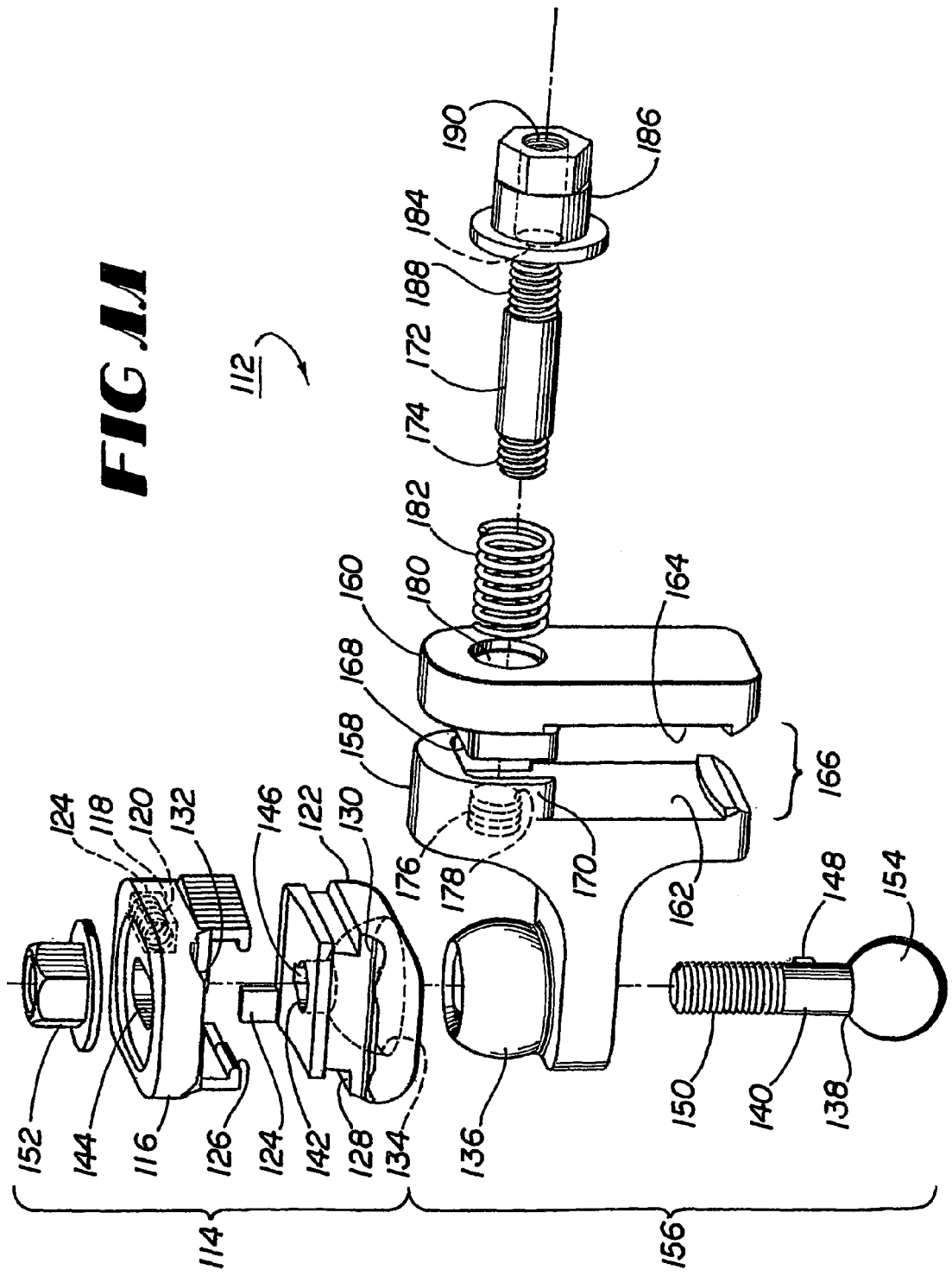
FIG. 11 is an exploded perspective view of the fixation component of FIG. 10.
Figure 12:
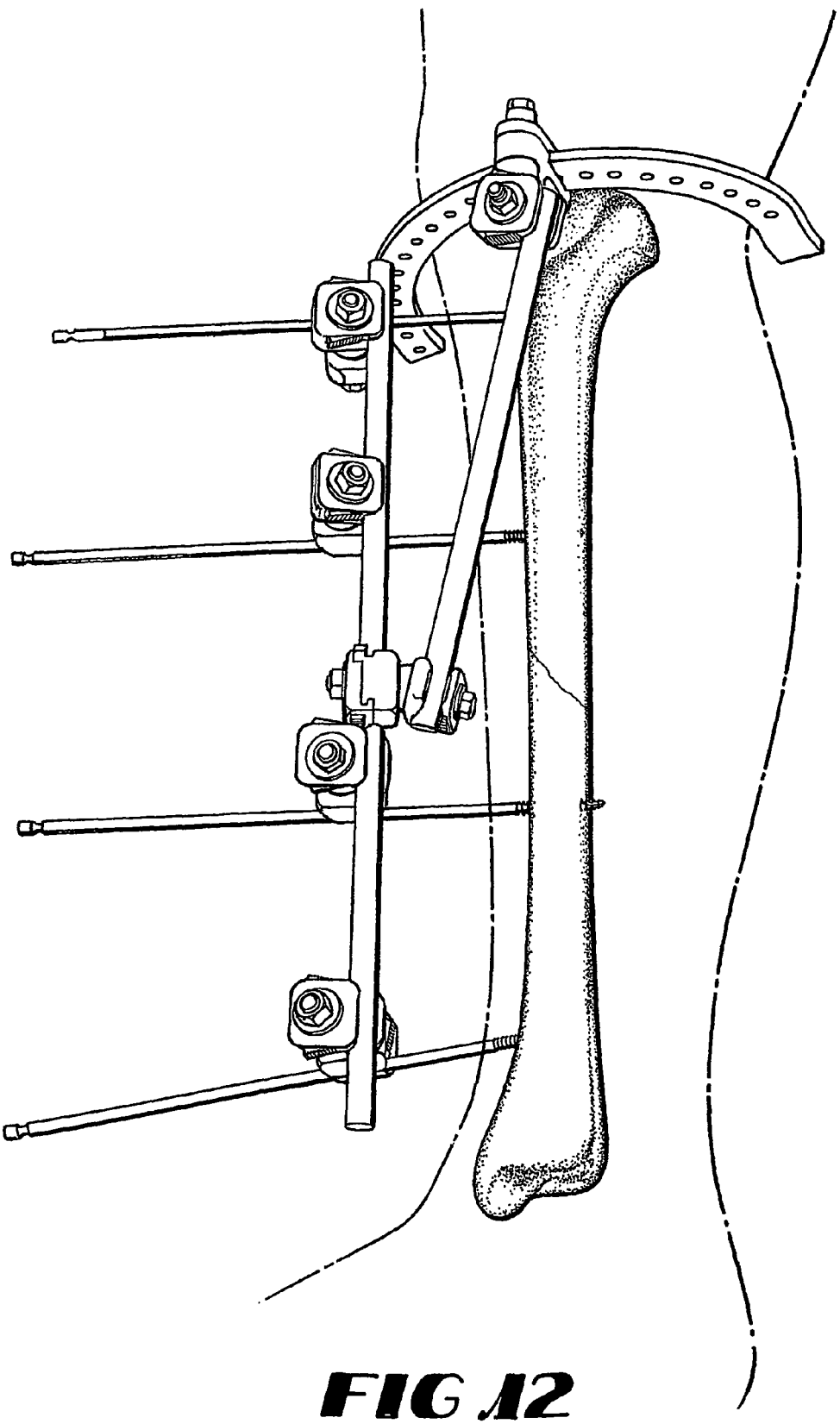
FIG. 12 is a perspective view of an external fixation system according to one embodiment of this invention.

Referring to FIGS. 10 and 11, a T-component 112 according to one embodiment of a fixation component of this invention includes a second capture member 114 that is similar to the second capture member described above with respect to the bar-to-pin fixation component. A head 116 of second capture member 114 has a recess 118 adapted to receive a spring 120, while a base 122 of second capture member 114 includes a stop 124. Recess 118 and spring 120 function as described above. Second capture member 114 also includes a first track 126 and a second track 128 so that head 116 and base 122 translate and retain a bar in a groove 130 and a wedge 132 in the same manner as described above.

Base 122 of second capture member 114 also includes a cooperating surface 134, which is adapted to receive a planetary member 136 of a first capture member 156. A connector 138, which, as described above and shown in FIG. 11, may be a ball stud, has a shaft 140 that extends through apertures 142 and 144 in base 122 and head 116, respectively, of second capture member 114. A slot 146 in aperture 142 of base 122 is adapted to receive a key 148 on shaft 140 of connector 138 in order to prevent rotation of connector 138 within second capture member 114. Threads 150 on shaft 140 mate with a second fastener 152, while an end 154 is received in planetary member 136.

First capture member 156 includes a base 158 and a head 160, each having a recess 162 and 164, respectively, that together form a channel 166, adapted to receive a ring having a rectangular cross-section. Head 160 has an extension 168 that fits into a rim 170 of base 162. A rod 172 includes second threads 174 that mate with internal threads 176 of an aperture 178 of base 158 after extending through an aperture 180 of head 160. A biasing element 182, such as a spring, passes over rod 172 and also into an aperture 184 of a first fastener 186. First threads 188 of rod 172 mate with internal threads 190 of first fastener 186. Tightening of first fastener 186 thus locks base 158 and head 160 of first capture member 156. Second capture member 114 is free to rotate about planetary member 136 of base 158 of first capture member 156 until second fastener 152 is tightened, at which time both second capture member 114 and planetary member 136 and cooperating surface 134, which form the joint, are locked.

In an alternative embodiment, other locking mechanisms may be used, such as a universal joint mechanism, which allows independent movement in different directions. In yet another alternative embodiment, the capture member may include a flip through for the bar or pin, rather than a snap-on from the side as described above.

One embodiment of a fixation component of this invention is made from titanium and aluminum. In this embodiment, the heads of the capture members are made from aluminum and the remaining parts from titanium. In alternative embodiments, fixation components are made from metals, alloys, plastics, composites, ceramics, or any other suitable material.

Figure 14:
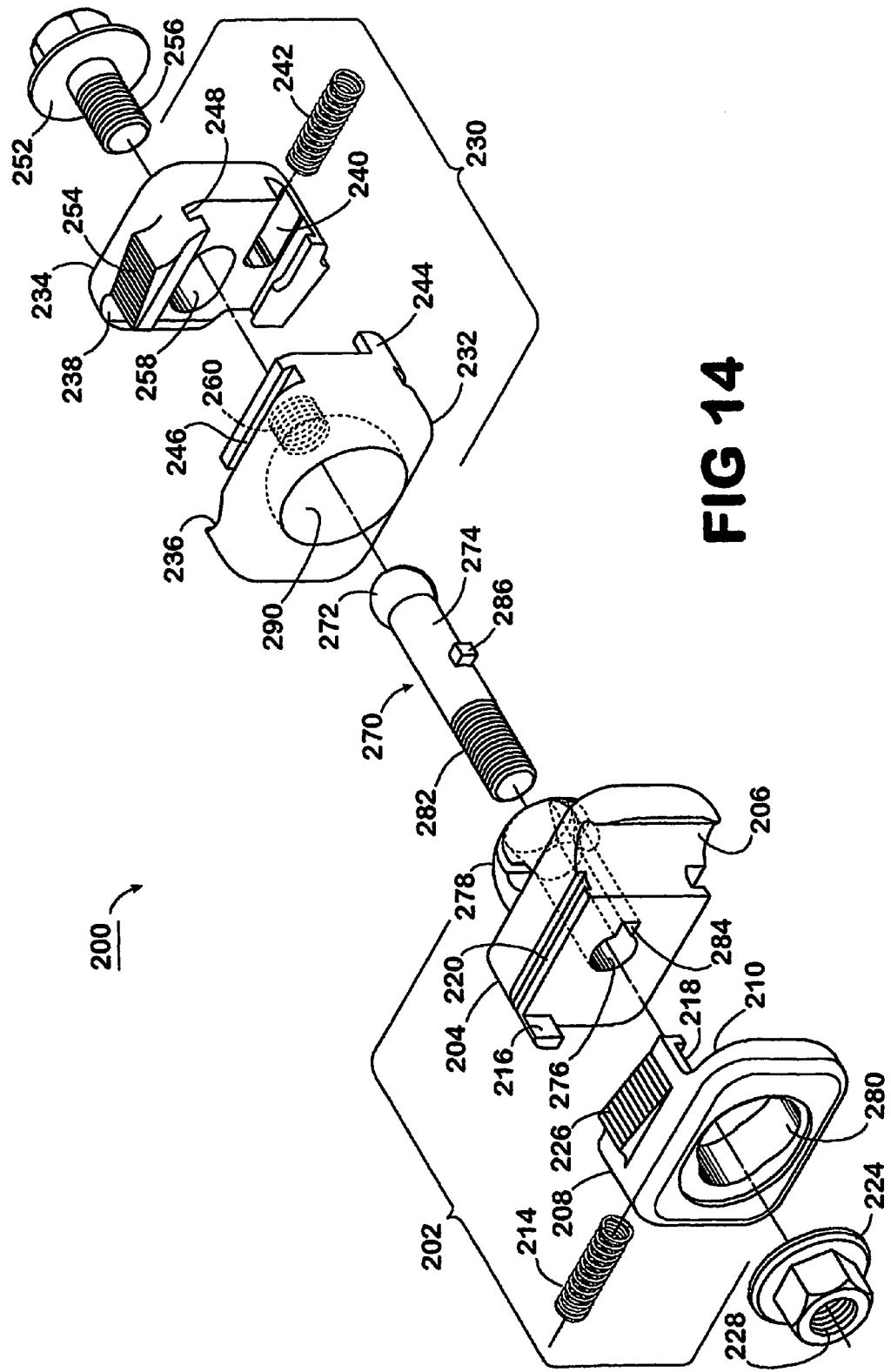
FIG. 14 is an exploded perspective view of an alternative embodiment of this invention.
Figure 15:
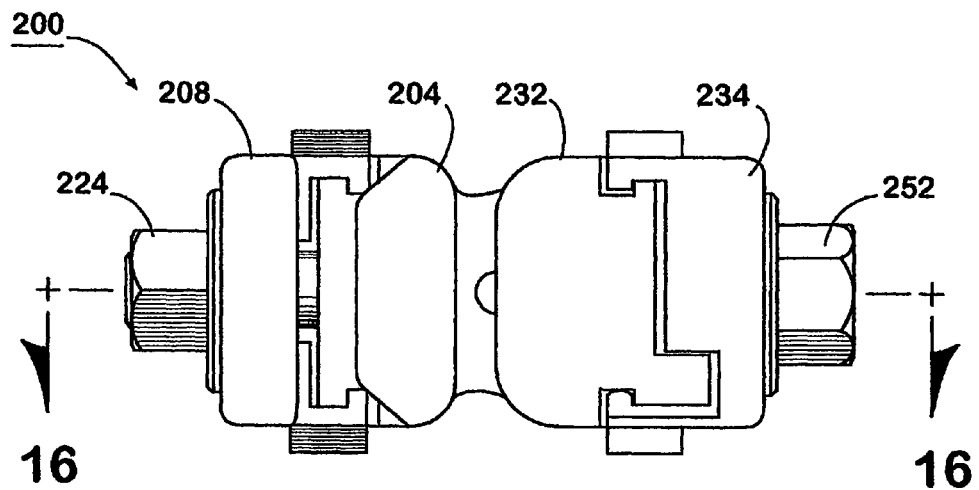
FIG. 15 is a plan view of the fixation component of FIG. 14.
Figure 16:
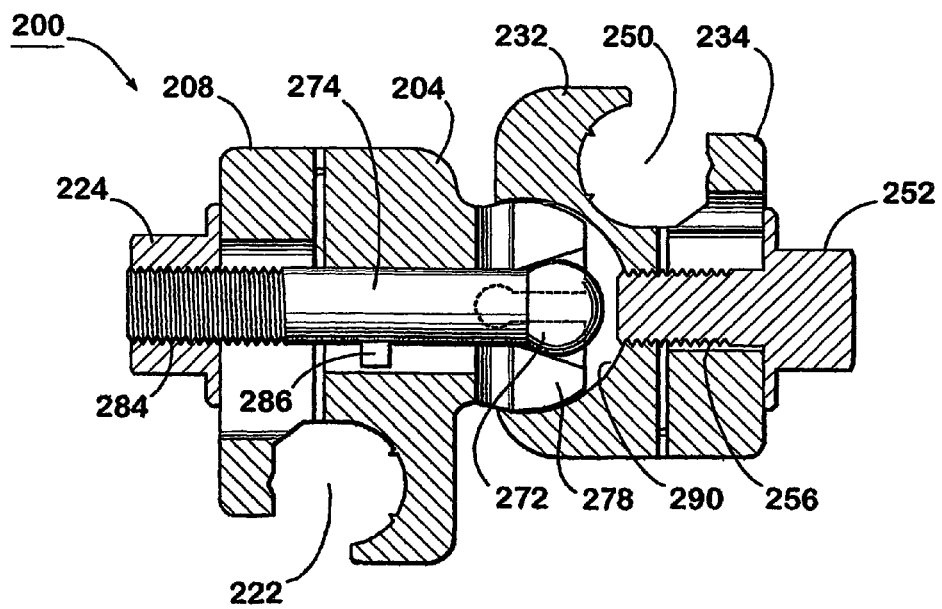
FIG. 16 is a cross-sectional view of the fixation component of FIG. 14 taken along lines 16-16 of FIG. 15.
Figure 17:
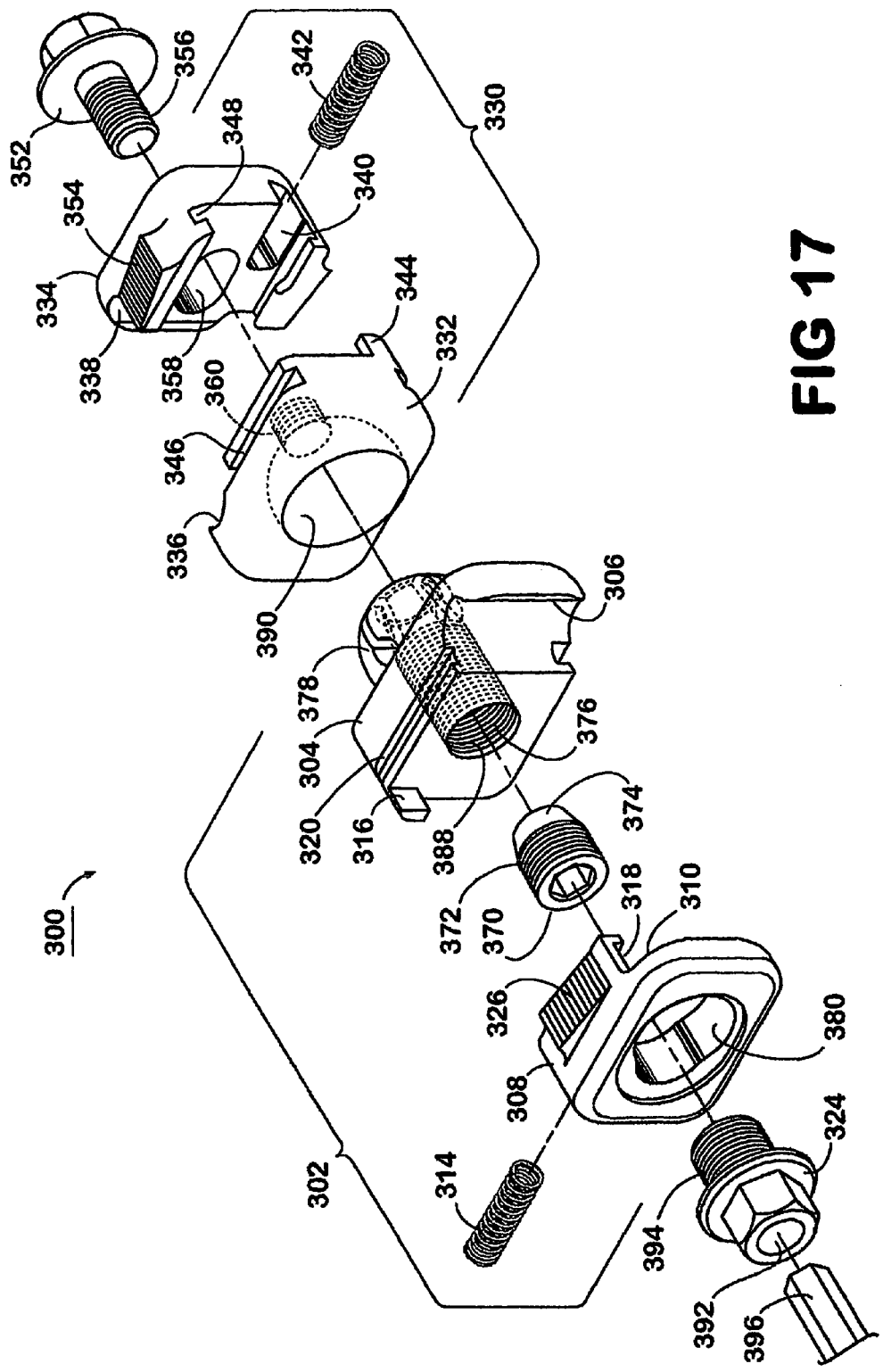
FIG. 17 is an exploded perspective view of an alternative embodiment of this invention.
Figure 18:
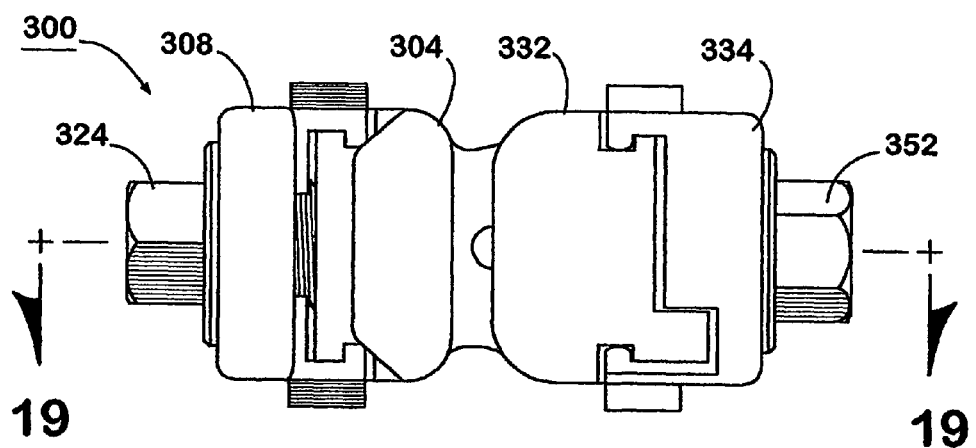
FIG. 18 is a plan view of the fixation component of FIG. 17.
Figure 19:
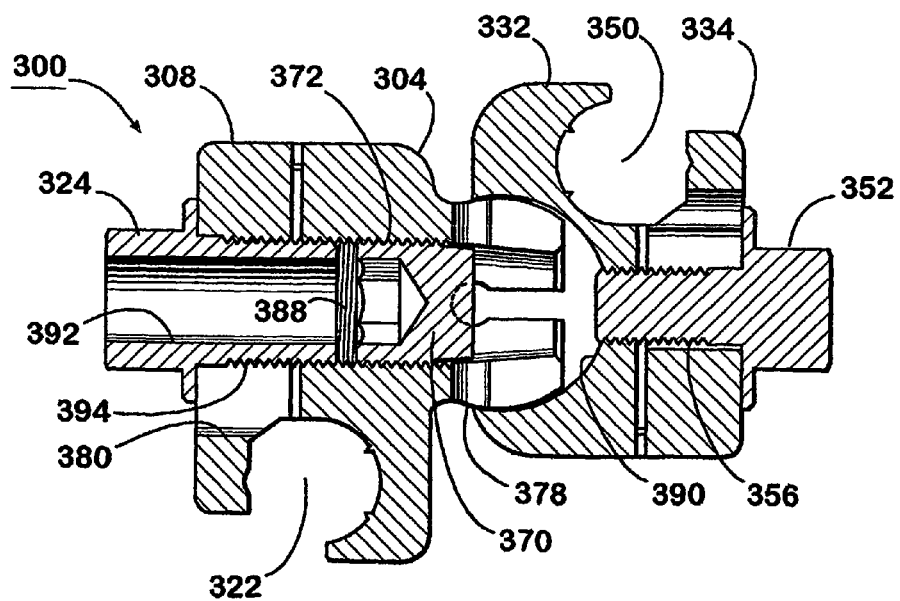
FIG. 19 is a cross-sectional view of the fixation component of FIG. 17 taken along lines 19-19 of FIG. 18.

As noted above, additional alternative embodiments of capture members and a joint mechanism between two capture members are shown in FIGS. 14-19. One alternative joint mechanism is shown in FIGS. 14-16, while another alternative is shown in FIGS. 17-19. The capture members shown in FIGS. 14-19 generally perform in a similar manner as the capture members described above with regard to the receipt of fixation elements and engagement of the base and head of each capture member.

As shown in FIGS. 14-16, a fixation component 200 includes a first capture member 202 and a second capture member 230. Capture members 202 and 230 may be designed to retain one of any of a pin, wire, bar, at least a partial ring, or other fixation element. As shown in FIGS. 14-16, each capture member is designed to receive a bar. A base 204 of first capture member 202 includes a groove 206, while a head 208 of first capture member 202 contains a wedge 210, which together are adapted to retain a fixation element. Likewise, a base 232 and a head 234 of second capture member 230 include a groove 236 and a wedge 238, together adapted to retain a fixation element in the same manner as described above.

Head 208 of first capture member 202 has a recess (not shown) adapted to receive a spring 214, while base 204 of first capture member 202 includes a stop 216. The recess, spring 214, and stop 216 function in the same manner as described above. First capture member 202 also includes a first track 218 and a second track 220 so that head 208 and base 204 translate and retain a fixation element in a channel 222 formed by groove 206 and wedge 210 in the same manner as described above. The angular position of channel 222 is set by tightening a first fastener 224. Prior to tightening of first fastener 224, the cartridge mechanism, in the loosened state, does not allow an inserted fixation element to passively separate or detach from capture member 202.

Second capture member 230 also includes a cartridge mechanism for retaining a fixation element. Head 234 of second capture member 230 has a recess 240 adapted to receive a spring 242, while base 232 of second capture member 230 includes a stop 244. Second capture member 230 also includes a first track 246 and a second track 248 so that head 234 and base 232 translate and retain a fixation element in a channel 250 formed by groove 236 and wedge 238 in the same manner as described above. The angular position of channel 250 is set by tightening a second fastener 252. Prior to tightening of second fastener 252, the cartridge mechanism, in the loosened state, does not allow an inserted fixation element to passively separate or detach from capture member 230.

In the embodiments shown, the recess, spring, and stop are located on one side of the capture member. In an alternative embodiment, the recess, spring, and spring stop are in the middle of the capture member, or are on the other side of the capture member. In one embodiment, heads 208 and 234 of capture members 202 and 230, respectively, include grip surfaces 226 and 254 for gripping and sliding heads 208 and 234 in relation to bases 204 and 232, respectively. In one embodiment, grip surfaces 226 and 254 include ridges.

A threaded end 256 of second fastener 252 passes through an aperture 258 in head 234 of second capture member 230, mating to internal threads 260 in base 232 of second capture member 230. Tightening of second fastener 252 locks second capture member 230 and rigidly retains an inserted fixation element.

A connector 270 having an end 272 and a shaft 274 extends through bore 276 in base 204 of first capture member 202. In one embodiment, connector 270 is a ball stud, as shown in FIG. 14, having a spherical end. End 272 of connector 270 is received in a spherical collet 278 of base 204 of first capture member 202. Shaft 274 of connector 270 extends through bore 276 in base 204 of first capture member 202 and an aperture 280 in head 208 of first capture member 202, and mates with first fastener 224. Threads 282 on shaft 274 of connector 270 mate with internal threads 228 of first fastener 224. A slot 284 in bore 276 of base 204 of first capture member 202 is adapted to receive a key 286 on shaft 274 of connector 270. Key 286 and slot 284 thus prevent rotation of connector 270 within first capture member 202.

The end of bore 276 may be tapered or countersunk. When connector 270 is inserted through the countersunk end of bore 276 and aperture 280 of head 208 of first capture member 202, end 272 rests against the countersunk end of bore 276. First fastener 224 is threaded onto shaft 274 so that as first fastener 224 is tightened against capture member 202, end 272 is pulled through base 204 and head 208 of capture member 202, forcing spherical collet 278 to expand.

A spherical pocket 290 of base 232 of second capture member 230 receives spherical collet 278. In a loosened state (i.e., first fastener 224 is not fully tightened and spherical collet 278 is not fully expanded), spherical collet 278 may be retained within spherical pocket 290, and spherical collet 278 may or may not be biased against spherical pocket 290 to provide resistance for the joint mechanism. When end 272 of connector 270 is not expanding spherical collet 278, capture members 202 and 230 may be rotated about or detached from each other. When first fastener 224 is tightened and spherical collet 278 fully expanded, capture members 202 and 230 cannot be rotated about each other or detached from each other. The tightening of first fastener 224 locks first capture member 202 and the joint to make it rigid. In one embodiment, one or both of the spherical collet and spherical pocket may be tapered. For example, a taper of 10°, 15°, 20°, or 30° may be used on each. Several mechanisms may be used to improve the locking capabilities of the joint, including coatings, elastic materials, or alternate taper shapes as discussed above.

The joint mechanism shown in FIGS. 14-16 allows the first capture member to rotate with respect to the spherical pocket of the second capture member, and allows the second capture member to grasp and lock a fixation element while permitting the first capture member to continue to rotate. Independent tightening of the capture members provides the surgeon flexibility to snap a fixation element to a capture member and then to manipulate the first capture member before locking the first capture member in order to achieve a more stable frame. In this manner, independent tightening of each capture member of the external fixation component allows more precise angular positioning.

In addition to increasing the degrees of freedom of movement of fixation components and allowing for more precise angular positioning, the use of the joint mechanism shown in FIGS. 14-16 provides a modular external fixation system for use by surgeons. Rather than providing pre-assembled fixation components in a surgical tray, separate capture members, not yet attached to other capture members to form fixation components, may be provided. For example, instead of providing a predetermined number of bar-to-bar fixation components and bar-to-pin fixation components in a surgical tray, a system may include a specified number of capture members for receiving bars and capture members for receiving pins. The capture members may be connected by the surgeon, or an assistant, using the joint mechanism shown in FIGS. 14-16 to form specific fixation components (e.g., bar-to-bar, bar-to-pin, bar-to wire, etc.) as desired based upon the surgery being performed. This provides better inventory control and should reduce the number of capture members and/or fixation components required to be provided in a surgical tray.

Another alternative embodiment is shown in FIGS. 17-19. Similar to the embodiment shown in FIGS. 14-16, the embodiment shown in FIGS. 17-19 also provides better inventory control by using capture members that may be easily detached and interchanged with other capture members to form the type of fixation component desired. However, the embodiment shown in FIGS. 17-19 also provides independent locking of the joint and each capture member rather than providing the simultaneously locking of the joint and one of the two capture members as discussed with regard to several other embodiments.

As shown in FIGS. 17-19, a fixation component 300 includes a first capture member 302 and a second capture member 330. Capture members 302 and 330 may be designed to retain one of any of a pin, wire, bar, at least a partial ring, or other fixation element. As shown in FIGS. 17-19, each capture member is designed to receive a bar. A base 304 of first capture member 302 includes a groove 306, while a head 308 of first capture member 302 contains a wedge 310, which together are adapted to retain a fixation element. Likewise, a base 332 and a head 334 of second capture member 330 include a groove 336 and a wedge 338, together adapted to retain a fixation element in the same manner as described above.

Head 308 of first capture member 302 has a recess (not shown) adapted to receive a spring 314, while base 304 of first capture member 302 includes a stop 316. The recess, spring 314, and stop 316 function in the same manner as described above. First capture member 302 also includes a first track 318 and a second track 320 so that head 308 and base 304 translate and retain a fixation element in a channel 322 formed by groove 306 and wedge 310 in the same manner as described above. The angular position of channel 322 is set by tightening a first fastener 324. Prior to tightening of first fastener 324, the cartridge mechanism, in the loosened state, does not allow an inserted fixation element to passively separate or detach from capture member 302.

Second capture member 330 also includes a cartridge mechanism for retaining a fixation element. Head 334 of second capture member 330 has a recess 340 adapted to receive a spring 342, while base 332 of second capture member 330 includes a stop 344. Second capture member 330 also includes a first trick 346 and a second track 348 so that head 334 and base 332 translate and retain a fixation element in a channel 350 formed by groove 336 and wedge 338 in the same manner as described above. The angular position of channel 350 is set by tightening a second fastener 352. Prior to tightening of second fastener 352, the cartridge mechanism, in the loosened state, does not allow an inserted fixation element to passively separate or detach from capture member 330.

In the embodiments shown, the recess, spring, and stop are located on one side of the capture member. In an alternative embodiment, the recess, spring, and spring stop are in the middle of the capture member, or are on the other side of the capture member. In one embodiment, heads 308 and 334 of capture members 302 and 330, respectively, include grip surfaces 326 and 354 for gripping and sliding heads 308 and 334 in relation to bases 304 and 332, respectively. In one embodiment, grip surfaces 326 and 354 include ridges.

A threaded end 356 of second fastener 352 passes through an aperture 358 in head 334 of second capture member 330, mating to internal threads 360 in base 332 of second capture member 330. Tightening of second fastener 352 locks second capture member 330 and rigidly retains an inserted fixation element.

A set screw 370 including threads 372 is inserted into bore 376 in base 304 of first capture member 302. In one embodiment, set screw 370 is tapered. End 374 of set screw 370 is received in a spherical collet 378 of base 304 of first capture member 302. Threads 372 on set screw 370 mate with internal threads 388 of bore 376 of base 304 of first capture member 302.

A spherical pocket 390 of base 332 of second capture member 330 receives spherical collet 378. When set screw 370 is tightened, spherical collet 378 expands and the joint between first and second capture members 302 and 330 is rigid. In a loosened state, when set screw 370 is not tightened, spherical collet 378 may be retained within spherical pocket 390, and spherical collet 378 may or may not be biased against spherical pocket 390 to provide resistance for the joint mechanism. Locking of the joint between the two capture members prevents rotation of either capture member about each other, but neither capture member is locked by tightening of set screw 370. When set screw 370 is partially threaded onto internal threads 388 of base 304 of first capture member 302 and spherical collet 378 is within spherical pocket 390 but not fully expanded, capture members 302 and 330 may be rotated about each other. Several mechanisms may be used to improve the locking capabilities of the joint, including coatings, elastic materials, or alternate taper shapes as discussed above.

First fastener 324 includes a bore 392 and threads 394. First fastener 324 extends through an aperture 380 in head 308 of first capture member 302 and threads 394 are threaded onto internal threads 388 of base 304 of first capture member 302. Tightening of first fastener 324 locks capture member 302. Bore 392 extends through first fastener 324, allowing for insertion of a tool 396 to tighten or loosen set screw 370 in spherical collet 378.

Figure 13:
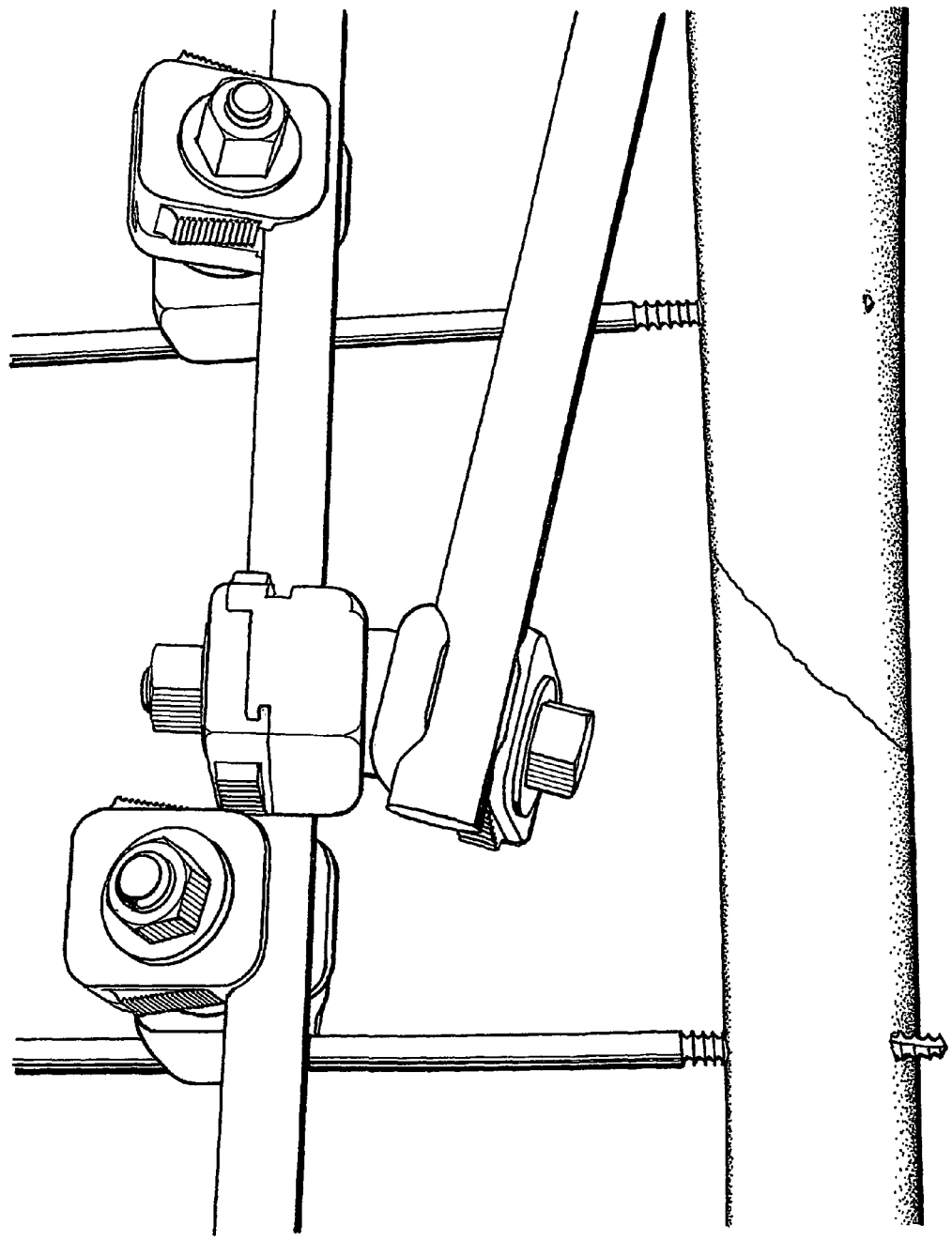
FIG. 13 is an enlarged fragmentary perspective view of selected fixation components of FIG. 12.

One method of using one form of structure according to this invention, shown in FIG. 13, is as follows:

At least two half pins are self-drilled into a bone, one on either side of a bone fracture. One bar-to-pin fixation component is connected to each pin by placing each pin into the capture member of each fixation component sized to receive a pin, such as the first capture member of the bar-to-pin fixation component shown in FIG. 1. Each fixation element is placed into the fixation component from the side for easy placement. After a pin is in place, the first fastener is tightened, so that the pin is retained in the capture member, while the second capture member and joint continue to freely rotate. Bars are then snapped into the bar capture member of the fixation components, forming a frame for the system. As each bar is added, the fixation components are adjusted as required by loosening the joint and second capture member, so that optimal positioning may be obtained. Bar-to-bar fixation components and bar-to-pin fixation components may be added to expand and connect the frame as required. If it is necessary or desirable to utilize a circumferential ring or half ring with a system for complex fractures, as shown in FIG. 13, additional fixation components having capture members designed to retain the rectangular bar of a ring are used to join the standard system to the specialized frame. A T-component is used to capture the rectangular bar of a ring and link it to a bar of the original frame, forming a hybrid system. If additional reduction is required, one capture member of any component may be loosened without losing placement of the system. A T-component may also be used to provide stability to an existing system that has already been placed using standard fixation component designs. A plurality of clamps may be used in various configurations to achieve stability for different fractures.

Similar instrumentation and devices may be used in other areas, such as to provide a fixed reference to a pin. Constructs made under the present invention are stable and provide for a wide variety or placements. Embodiments of an external fixation component according to this invention may also be adapted for use with an image guided surgery system to provide stability to a reference frame or other guidance target or mechanism.

The foregoing description of certain exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and certain exemplary embodiments described therein.

The invention claimed is:

1. A capture member for retaining a fixation element of an external fixation system, the capture member comprising:
    a base comprising a groove disposed along a side of the base and a base track disposed substantially perpendicular to the groove;
    a head comprising a wedge disposed along a side of the head in registry with the groove of the base and a head track slidably coupled to the base track, wherein the wedge and groove of the head and the base form a channel configured to receive a fixation element; and
    the base and head tracks slidably coupling the base and the head and holding the fixation element in the channel formed between the base and the head, the capture member further comprising an elastic element acting on at least one of the head and the base such that as a force perpendicular to a fixation element is exerted against the channel formed by the base and the head, the elastic element compresses until the elastic element exerts a force in a direction perpendicular to the fixation element that is equal and opposite to the force exerted against the channel, thereby holding the fixation element positioned within the channel in place, and wherein at least one of the groove and the wedge includes splines.

2. The capture member of claim 1, wherein the elastic element is positioned within a recess in at least one of the head and the base.

3. The capture member of claim 2, comprising at least two elastic elements positioned in recesses in at least one of the head and the base and acting on at least one of the head and the base.

4. The capture member of claim 3, wherein the recesses and elastic elements are located in the middle of the capture member.

5. The capture member of claim 3, wherein the recesses and elastic elements are located in the sides of the capture member.

6. The capture member of claim 1, wherein said base has at least two base tracks and said head has at least two head tracks slidably coupled to allow for movement between said base and said head.

7. The capture member of claim 1, wherein the head track slides in the base track.

8. The capture member of claim 1, wherein the base track slides in the head track.

9. The capture member of claim 1, wherein one of the base track and head track is an L-shaped track and the other is shaped to receive the L-shaped track.

10. The capture member of claim 1, wherein the base is provided with an elevated portion providing a point of contact between the base and the head in order to increase the holding power of the fixation element by the capture member.

11. The capture member of claim 1, wherein the head is provided with a grip surface to assist in slidably moving the head with respect to the base.

12. The capture member of claim 11, wherein the grip surface comprises a plurality of ridges.

13. The capture member of claim 1, wherein at least one of the base and head is provided with an aperture.

14. The capture member of claim 13, wherein the aperture is at least one of a keyhole and a slot.

15. The capture member of claim 14, wherein the major diameter of the at least one of the keyhole and a slot is perpendicular to the axis of the fixation element.

16. The capture member of claim 14, further comprising a fastener having a reduced diameter neck inserted through the aperture though at least one of the head and base and said fastener being affixed to the opposite of the at least one of the base and head of the capture member.

* * * * *